United States Patent [19]
Lampert

[11] 4,263,715
[45] Apr. 28, 1981

[54] METHOD AND APPARATUS FOR MOUNTING DENTAL MODELS ON ARTICULATORS

[75] Inventor: Barry Lampert, Huntington, N.Y.
[73] Assignee: Rab Tec Products Corporation, Freeport, N.Y.
[21] Appl. No.: 803,201
[22] Filed: Jun. 3, 1977
[51] Int. Cl.² .......................................... A61C 17/04
[52] U.S. Cl. ....................................... 433/60; 433/66
[58] Field of Search ......................................... 32/32

[56] References Cited

U.S. PATENT DOCUMENTS

| | | | |
|---|---|---|---|
| 2,094,903 | 10/1937 | Pittman et al. | 32/32 |
| 2,550,043 | 4/1951 | De Lautour | 32/32 |
| 2,952,914 | 9/1960 | Shackelford | 32/32 |
| 3,808,689 | 5/1974 | Spinella | 32/32 |
| 3,885,311 | 5/1975 | Lawler et al. | 32/32 |

FOREIGN PATENT DOCUMENTS 2053294  5/1972  Fed. Rep. of Germany .............. 32/32

*Primary Examiner*—Russell R. Kinsey
*Assistant Examiner*—John J. Wilson
*Attorney, Agent, or Firm*—Feldman & Feldman

[57] ABSTRACT

A mounting plate is formed from plastic and with a first one of its planar surfaces substantially flat and otherwise formed to be affixed to a dental model. A connecting rib, formed to extend out from the other planar surface of the mounting plate, and along its entire length, has a modified "T" shaped configuration with a vertical leg extending up from the planar surface and a cross-arm extending out to each side of the leg so as to form a groove to each side of the vertical leg between the planar surface of the plate and the opposed surface of the cross-arm. A slot is formed through the central rib of each articulator with a shoulder extending from each wall of the slot into the slot but so as to leave a narrow passage sized to receive the vertical leg of the modified "T" shaped rib. The grooves formed between the cross-arm of the rib and the plate surface, in turn, receive the shoulders that extend into the slots, all so as to tightly receive the connecting rib of the mounting plate and firmly but removably secure the mounting plate, and any dental mold affixed thereto to one of the bows of the dental articulator.

4 Claims, 6 Drawing Figures

U.S. Patent        Apr. 28, 1981        4,263,715
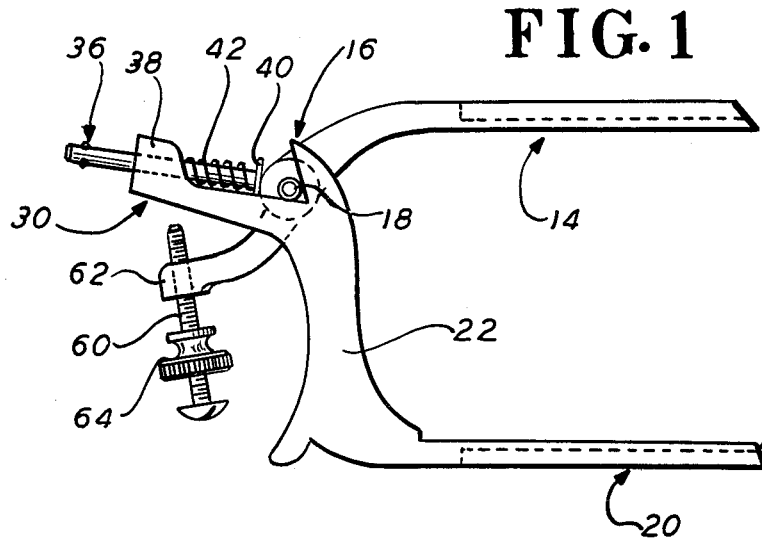
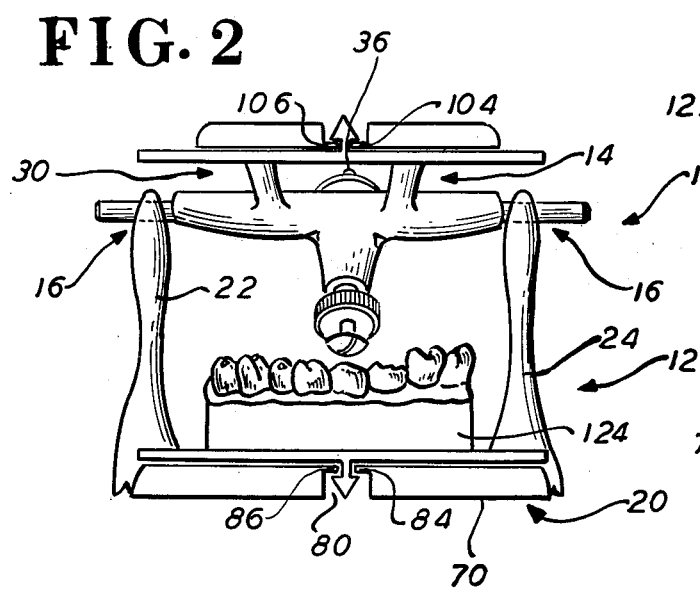
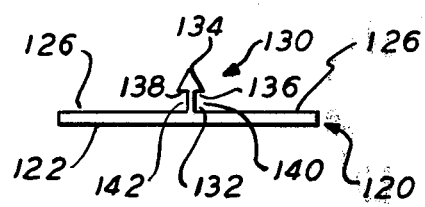
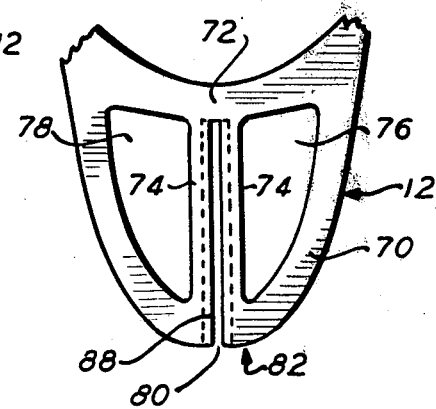
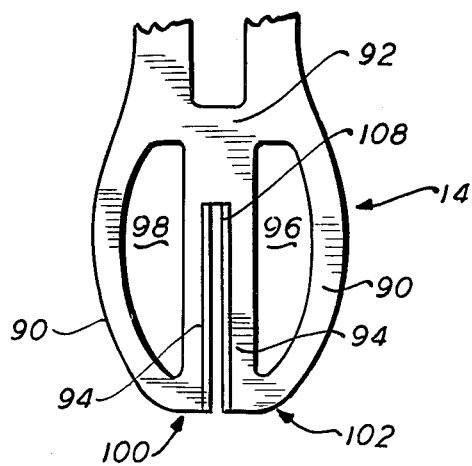
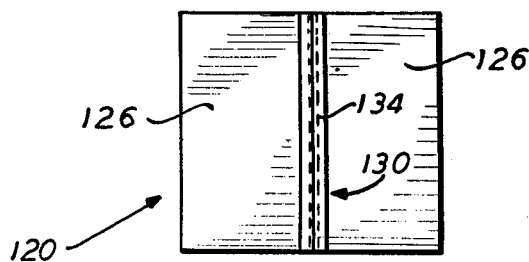

4,263,715

METHOD AND APPARATUS FOR MOUNTING DENTAL MODELS ON ARTICULATORS

BACKGROUND OF THE INVENTION

1. Field of Application

This invention relates to dental articulators; and more particularly to a method and apparatus for removably affixing a dental model to the dental articulator.

2. Description of the Prior Art

Dental articulators are widely used today in the fabrication and servicing of artificial teeth or dentures as they are more commonly known; and otherwise for dental restoration work. Such work is usually performed by skilled dental artisians and is tedious, arduous and very time consuming. Obviously, it is much easier, and absolutely essential, for the dental artisian to work with a dental model of his patient rather than directly in the patient's mouth; except for final fittings and adjustments.

To allocate an articulator for each dental model would require not only an unduly large number of articulators; but would necessitate tying up a lot of funds in the unnecessary duplication of equipment. In addition, space is expensive and the storage of the articulator with each dental model set must increase the amount of storage space required in the dental lab or office.

Some prior art articulators, such as those shown in U.S. Pat. No. 2,365,475 issued on Dec. 19, 1944 to I. Klein for Dental Mounting Service and in U.S. Pat. No. 2,629,929 issued on Mar. 3, 1953 to C. Levine, et al., for Mounting For Artificial Dentures provide apparatus for separating the dental model from the articulator, and for properly replacing same. As such one articulator can serve many dental models. However, each of these systems requires the use of plaster molding to secure the plate to the articulator; and a relatively complex system of aligning apertures, lugs, threaded securing elements and the use of securing pins that have to be inserted through small holes in tight places. All of this is tedious and cumbersome. In addition plaster cracks and falls away to possibly loosen the bond between the plate and articulator bow and to distort the aligning apertures; while holes may fill up with plaster and be difficult, if not impossible to clean out.

Other prior art approaches to the problem utilize a mounting plate which is secured to the dental model and which has locating apertures and/or lugs, that co-operate with corresponding apertures or lugs on the articulator; as well as an internally threaded aperture which receives an externally threaded number carried by the articulator. Such mechanisms are exemplified by the showings in U.S. Pat. No. 3,123,914 issued on Mar. 10, 1964 to A. J. De Pietro for Mounting Plate; U.S. Pat. No. 3,750,289 issued on Aug. 7, 1973 to Niles F. Guichet for Centric Relating Device; U.S. Pat. No. 3,965,576 issued on June 29, 1976 to Melbourne D. Eveland for Dental Apparatus and Method; and U.S. Pat. No. 3,908,271 issued on Sept. 30, 1975 to Henry J. Derda for Dental Articulator. All of these still require locating pins and apertures with their aforementioned shortcomings, at least one internally threaded bore and a correspondingly externally threaded member. Damage to the threads of either member, the accumulation of plaster on the threads and loss of the externally threaded member all dictate against the purported value of this type of apparatus and system.

SUMMARY OF THE INVENTION

It is therefore an object of this invention to provide a new and improved method of removably securing a dental model to a dental articulator.

It is another object of this invention to provide a new and improved apparatus for removably securing a dental model to a dental articulator.

It is yet another object of this invention to provide a new and improved means for removably securing a dental model plate to a dental articulator.

It is still another object of this invention to provide a new and improved dental articulator and mounting plate combination.

It is a further object of this invention to provide a new and improved dental model mounting plate.

This invention involves dental articulators; and contemplates forming the bow members thereof with a slot which receives a rib of a dental model mounting plate to removably secure a dental model mounting plate in position on each bow of a dental articulator.

Other objects, features, and advantages of the invention in its details of construction and arrangement of parts will be seen from the above, from the following description of the preferred embodiments when considered with the drawings and from the appended claims.

BRIEF DESCRIPTION OF THE DRAWING

In the drawing:

FIG. 1 is a side elevational view of a dental articulator incorporating the instant invention;

FIG. 2 is a front elevational view of the dental articulator of FIG. 1 with a dental model in position on the lower bow thereof and mounted to a dental model mounting plate incorporating the instant invention.

FIG. 3 is a partial plan view of the lower bow member of the articulator of FIGS. 1 and 2;

FIG. 4 is a partial plan view of the upper bow member of the articulator of FIGS. 1 and 2;

FIG. 5 is a plan view of the dental model mounting plate; and

FIG. 6 is an end view of the dental model mounting plate of FIG. 5.

DESCRIPTION OF THE PREFERRED EMBODIMENT

For convenience the invention will be described as applied to a dental articulator made from aluminum and with upper and lower bow members each formed with peripheral ribs and a central rib, and with a single shouldered slot cut into each central rib. A dental model mounting plate is formed from vinyl plastic, of a size proximate that of each bow member, and with a modified "T" shaped rib extending the length of the plate; and of a size and configuration to co-operate with the slot in the bow member so as to provide for removable securing of the plate to said bow member. It should be understood, nevertheless, that without departing from the scope of this invention, that other suitable materials can be used for both the articulator and mounting plate, that the bows of the articulator may be otherwise formed, that more then one slot may be provided on each bow of the articulator and a corresponding member of ribs provided on each plate.

With reference to FIGS. 1 and 2, there is generally shown at 10 a dental articulator of somewhat conventional construction and design and substantially formed from aluminum or other similar suitable material. A lower jaw member 12 of articulator 10 pivotally mounts an upper jaw member 14 by means of a pin 16 carried by upper jaw member 14. Pin 16 pivotally rests in seats 18 (FIG. 1) and 20 (FIGS. 1 and 2) formed by notches provided at the junctures of upwardly extending legs 22, 24 of lower jaw member 12 and an arm 30 which extends from both legs 22, 24. A pressure pin 36, slidably disposed in an aperture formed through a boss 38 carried by arm 30, is formed with a head 40 (FIG. 1) and so as to have a spring 42 wound about its shank and lodged between head 40 and boss 38. Spring 42, when so disposed, urges head 40 of pressure pin 36 against upper jaw 14 to seat pin 16 thereof in seats 18 and maintain upper jaw 14 in pivotal relationship with lower jaw 12.

An externally threaded member, such as a bolt 60, is threaded into an internally threaded boss 62 formed on upper jaw 14 and is fitted with a stop 64. Adjustment of bolt 60, and its co-action with the underside of arm 30 of lower jaw member 12, serves to adjust the position of upper jaw member 14 to lower jaw member 12.

Lower jaw member 12 is formed to include a lower bow portion formed by a peripheral rib 70, a cross rib 72 and a longitudinally extending central rib 74; all arranged to provide a pair of apertures 76, 78. A slot 80 is cut into longitudinally extending central rib 74 from a leading edge 82 thereof up to cross rib 72. Slot 80 is cut so as to provide a pair of shoulders 84, 86 (FIG. 2) which extend into slot 80 but are spaced from each other to provide a slit 88.

In similar manner upper jaw member 14 (FIGS. 2 and 4) is formed to include an upper bow portion formed by a peripheral rib 90, a cross rib 92, and a longitudinally extending central rib 94; all arranged to provide a pair of apertures 96, 98. A slot 100 is cut into longitudinally extending central rib 94 from a leading edge 102 thereof up to cross rib 92. Slot 100, like slot 80, is cut so as to provide a pair of shoulders 104, 106 (FIG. 2) which extend into slot 100 but are spaced from each other to provide a slit 108.

A dental model mounting plate 20 (FIGS. 5 and 6), formed from vinyl plastic or other suitable material, is formed to a size approximating that of bow members 12, 14. A first substantially planar surface 122 (FIG. 6) of plate 120 is formed to be substantially flat and so as to be readily secured to a dental model 124 (FIG. 2) by conventionally available means such as epoxy or other suitable adhesive. A second substantially planar surface 126 of plate 120 includes an upstanding rib 130 in the form of a modified "T". Rib 130 includes a vertical leg 132 and a cross arm 134 which tops leg 132 and extends to both sides thereof forming shoulders 136, 138 substantially parallel to planar surface 126. As such a pair of grooves 140, 142 are formed between shoulders 136, 138 and planar surface 126. The size and configuration of of grooves 140, 142 is such as will enable them to receive a corresponding shoulder 84, 86 or 104, 106 of lower bow 70 or upper bow 90 respectively.

In use the technician, or other user, merely slides dental model mounting plate 120 onto its respective bow member (70 or 90). Vertical leg 132 of rib 130 of plate 120 slides into slit 88 (or 108) and shoulders 136, 138 of cross arm 134 span shoulders 84, 86 (or 104, 106) so that said shoulders 84, 86 (or 104, 106) are snugly lodged in grooves 140, 142 or rib 130. Model 124 is either already in place on plate 126 or may thereafter be disposed securely thereon. To remove dental model 124 from articulator 10 one need merely slide plate 120 so that rib 130 separate from slot 80 (100) and slit 88 (108). The width of slots 80 and 100 and slits 88 and 108 may be selected to provide a grip against rib 130 to prevent accidental dislodgement thereof.

From the above description it will thus be seen that there has been provided a novel and improved method and apparatus for removably mounting a dental model in a dental articulator; which method and apparatus utilizes a relatively inexpensive dental model mounting plate secured by a rib and groove to its respective bow member of the dental articulator.

It is understood that although I have shown the preferred form of my invention that various modifications may be made in the details thereof without departing from the spirit as comprehended by the following claims.

I claim:

1. A dental articulator, comprising:
  (a) a lower jaw;
  (b) an upper jaw pivotally mounted to said lower jaw;
  (c) a lower member carried by said lower jaw;
  (d) an upper member carried by said upper jaw;
  (e) at least one slot formed in said lower member so as to extend inwardly from an edge thereof and including at least one slot formed in said upper member so as to extend inwardly from an edge thereof, wherein said slots in said upper and lower members are each formed with shoulders extending from the sides thereof into the slot but so as to be spaced from each other to leave a slit therebetween; and
  (f) a dental model mounting plate for each member being formed with a rib and wherein the dental model mounting plate rib is formed as a modified "T" with the vertical leg thereof extending up from a planar surface of the dental model mounting plate and having a cross arm extending to each side of the vertical leg, said rib and slot being sized to releasably mount the mounting plate to the articulator.

2. The dental articulator of claim 1, wherein the cross arm forms a pair of grooves between itself and the planar surface of the mounting plate; and wherein the grooves are sized to accommodate and receive said shoulders formed in said slots of said upper and lower members.

3. The dental articulator of claim 1, wherein the mounting plate is formed from plastic.

4. The dental articulator of claim 3, wherein the plastic is vinyl.

* * * * *